United States Patent
Nataniel et al.

(10) Patent No.: US 8,119,251 B2
(45) Date of Patent: *Feb. 21, 2012

(54) POLYAMIDES

(75) Inventors: Tina Nataniel, St. Charles, IL (US);
Dwight D. Heinrich, Aurora, IL (US)

(73) Assignee: Henkel Corporation, Rocky Hill, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/203,939

(22) Filed: Sep. 4, 2008

(65) Prior Publication Data

US 2009/0042047 A1 Feb. 12, 2009

Related U.S. Application Data

(63) Continuation of application No. PCT/US2007/063838, filed on Mar. 13, 2007.

(60) Provisional application No. 60/785,560, filed on Mar. 24, 2006.

(51) Int. Cl.
*C08G 69/26* (2006.01)

(52) U.S. Cl. ............. 428/474.4; 156/325; 156/326; 156/327; 156/330.9; 156/331.1; 528/339.3

(58) Field of Classification Search ............. 528/339.3; 428/474.4; 156/325–327, 330.9, 331.1
See application file for complete search history.

(56) References Cited

U.S. PATENT DOCUMENTS

| | | | |
|---|---|---|---|
| 2,793,219 A | 5/1957 | Barrett et al. | |
| 2,955,121 A | 10/1960 | Myers et al. | |
| 4,062,820 A | 12/1977 | Mitchell, III et al. | |
| 4,066,587 A * | 1/1978 | Mains et al. | 525/420.5 |
| 4,122,229 A | 10/1978 | Mitchell, III et al. | |
| 4,151,155 A * | 4/1979 | Chaplick | 523/167 |
| 4,218,351 A | 8/1980 | Rasmussen | |
| 4,810,772 A | 3/1989 | Leoni et al. | |
| 7,001,979 B2 | 2/2006 | Scholl et al. | |
| 7,160,979 B2 * | 1/2007 | Nataniel et al. | 528/339.3 |
| 7,163,996 B2 * | 1/2007 | Nataniel et al. | 528/339.3 |
| 2003/0035948 A1 * | 2/2003 | Fujimaru et al. | 428/343 |
| 2005/0165211 A1 | 7/2005 | Nataniel et al. | |
| 2005/0228165 A1 | 10/2005 | Nataniel et al. | |
| 2009/0130041 A1 * | 5/2009 | MacQueen et al. | 424/64 |

FOREIGN PATENT DOCUMENTS

| | | |
|---|---|---|
| DE | 4233025 A1 | 4/1994 |
| JP | 63196625 A | 8/1988 |

OTHER PUBLICATIONS

International Search Report dated Aug. 16, 2007 for Application No. PCT/US2007/06338.

* cited by examiner

*Primary Examiner* — Leszek Kiliman
(74) *Attorney, Agent, or Firm* — Steven C. Bauman

(57) ABSTRACT

The reaction of dimer acids, $C_{10}$-$C_{20}$ dicarboxylic acids, and alkylene diamines having from 2 to 8 carbon atoms provides polyamides having good oil and solvent resistance, high heat resistance, flexibility, and relatively low melt viscosities.

37 Claims, No Drawings

POLYAMIDES

CROSS-REFERENCE TO RELATED APPLICATIONS

This application is a continuation under 35 USC Sections 365(c) and 120 of International Application No. PCT/US2007/063838, filed 13 Mar. 2007 and published 4 Oct. 2007 in English as WO 2007/112200, which claims priority from U.S. Provisional Application No. 60/785,560, filed 24 Mar. 2006, each of which is incorporated herein by reference in its entirety.

FIELD OF THE INVENTION

The invention relates to polyamides based on dimer acids, $C_{10}$-$C_{20}$ dicarboxylic acids, and alkylene diamines having from 2 to 8 carbon atoms.

BACKGROUND OF THE INVENTION

Polyamides are commonly used as components of adhesive, sealing or coating compositions to be used in applications that will be exposed to solvents, oils and the like. Such compositions therefore must be able to withstand repeated or prolonged exposure to such substances without significant deterioration of their properties. At the same time, however, it will generally be desirable for such polyamides to not soften or melt at elevated temperatures and to have good flexibility (e.g., resistance to cracking or breaking). Additionally, the melt viscosity of the polyamide must be sufficiently low that the polyamide can be easily manufactured and also applied to substrate surfaces (as a hot melt adhesive, for example) using conventional application equipment. Although polyamides in general have been known for many years, it has proven difficult to obtain polyamides having all the aforementioned properties in combination.

BRIEF SUMMARY OF THE INVENTION

The present invention provides polyamides having an exceptionally desirable combination of properties, including good flexibility, high heat resistance, and good resistance to solvents such as gasoline. The polyamides are formed by reacting a) an acid component comprising at least one dimerized $C_{12}$ to $C_{24}$ unsaturated fatty acid (dimer acid) and at least one $C_{10}$-$C_{20}$ dicarboxylic acid and b) an amine component comprising at least one alkylene diamine having from 2 to 8 carbon atoms (in particular, hexamethylenediamine). The polyamides of the invention are particularly useful for hot melt adhesive formulations which will come into contact with organic solvents or oils, such as in fuel filter applications.

DETAILED DESCRIPTION OF CERTAIN EMBODIMENTS OF THE INVENTION

In preferred embodiments of the present invention, the polyamide possesses all of the following characteristics: a viscosity at 225° C. of at least 30 poise but not greater than 90 poise (e.g., 55 to 90 poise) or alternatively not greater than 140 poise (e.g., 100 to 140 poise); a softening point of at least 182° C. (e.g., 182 to 196° C.); and excellent resistance to both European gasoline formulations and gasohol. Preferably, the polyamide additionally is hard (for example, having a Shore A hardness greater than 90), yet non-brittle and flexible (e.g., where a micro dogbone sample of the polyamide having a thickness of 50 mil exhibits an elongation value of at least 50%, more preferably at least 100%).

The acid component used to prepare the polyamides of the present invention contains one or more dimerized $C_{12}$ to $C_{24}$ unsaturated fatty acids. Suitable dimer acids may be produced by combining or condensing two moles of unsaturated monocarboxylic acid (the monocarboxylic acid molecules which react may be the same or different). Processes for the production of dimer acids are well known to the art and by way of illustration, reference may be had to U.S. Pat. Nos. 2,793,219 and 2,955,121. Thirty-six carbon ($C_{36}$) dimer acids obtained by the dimerization of an unsaturated $C_{18}$ acid such as oleic acid, linoleic acid, linolenic acid and mixtures thereof (e.g., tall oil fatty acids) are especially useful and advantageously employed for the preparation of the polyamides. Such dimer acids have as their principal component a $C_{36}$ dicarboxylic acid and typically have an acid value in the range 180-215, saponification value in the range 190-205 and neutral equivalent from 265-310. Dimer acids containing less than 30% by weight by-product acids including monobasic acids, trimer acids or higher polymer acids are especially useful for this invention. The dimer acids may also be hydrogenated prior to use and/or molecularly distilled or otherwise purified to increase the dimer content to 90% or more. In certain embodiments of the invention, for example, the dimerized acid product utilized as a dimer acid source contains no more than 6% monobasic acids (as measured by AOCS Tf 5-91), no more than 5% polybasic acids (i.e., compounds containing three or more carboxylic acid groups per molecule; as measured by AOCS Tf 5-91), and at least 90% dibasic acids (as measured by AOCS Tf 5-91). Highly or completely saturated dimer acids may be utilized. The dimerized acid product in certain embodiments may, for example, have an iodine value (Wijs) of not more than 20 or not more than 10 (as measured by AOCS Tg 1a-64). In one embodiment, one or more $C_{32\text{-}40}$ dimer acids (i.e., dicarboxylic acids containing 32 to 40 carbon atoms per molecules obtained by dimerization of unsaturated fatty acids, such as $C_{16}$-$C_{20}$ unsaturated fatty acids) are utilized.

The preferred starting acids for the preparation of the dimerized fatty acids used in this invention are oleic and linoleic acids, due to their ready availability and relative ease of polymerization. Mixtures of oleic and linoleic acids are found in tall oil fatty acids, which are a convenient commercial source of these acids. Fatty acids can be dimerized using various well-known catalytic and non-catalytic polymerization methods.

The acid component additionally contains one or more aliphatic dicarboxylic acids containing from 10 to 20 carbon atoms, wherein the two carboxylic acid functional groups are terminal (i.e., on each end of the carbon chain). In one embodiment, the aliphatic dicarboxylic acids contain from 14 to 20 carbon atoms. The incorporation of such long chain aliphatic dicarboxylic acids into a polyamide has been found to significantly improve the chemical and solvent resistance of the polyamide, as compared to a polyamide prepared using only dimer acids. Although branched or substituted aliphatic dicarboxylic acids can be utilized as the $C_{10}$-$C_{20}$ aliphatic dicarboxylic acid, linear (straight chain) dicarboxylic acids are generally preferred. Suitable aliphatic dicarboxylic acids for use in the present invention include, but are not limited to, compounds corresponding to the general formula HOOC—$R_1$—COOH where $R_1$ is a divalent, aliphatic, hydrocarbon radical having from 8 to 18 carbon atoms such as decanedioic acid (sebacic acid), undecanedioic acid, tridecanedioic acid (brassylic acid), dodecanedioic acid (1,10-decanedicarboxylic acid), tetradecanedioic acid (1,12-dodecanedicarboxylic acid), pentadecanedioic acid (1,13-tridecanedicarboxylic acid), hexadecanedioic acid (1,14-tetradecanedicarboxylic acid, thapsic acid), octadecanedioic acid (1,16-hexadecanedicarboxylic acid) and mixtures thereof. $R_1$ preferably is polymethylene, i.e., $-(CH_2)_n-$, wherein n is 8 to 18. In one embodiment of the invention, tetradecanedioic acid is one of the $C_{10}$ to $C_{20}$ aliphatic dicarboxylic acids or the only such dicarboxylic acid used in the acid component. In one embodiment, tetradecanedioic acid may comprise at least 50 mole % (in another embodiment, at least 80 equivalent %; in yet another embodiment, at least 90 equivalent %) of the $C_{10}$ to $C_{20}$ aliphatic dicarboxylic acids used. In certain embodiments of the invention, octadecanedioic acid is one of the $C_{10}$ to $C_{20}$ aliphatic dicarboxylic acids or the only such dicarboxylic acid used in the acid component. In one embodiment, octadecanedioic acid may comprise at least 50 equivalent % (in another embodiment, at least 80 mole %; in yet another embodiment, at least 90 equivalent %) of the $C_{10}$ to $C_{20}$ aliphatic dicarboxylic acids used. In other embodiments of the invention, decanedioic acid is one of the $C_{10}$ to $C_{20}$ aliphatic dicarboxylic acids or the only such dicarboxylic acid used in the acid component. In another embodiment, decanedioic acid may comprise at least 50 equivalent % (in another embodiment, at least 80 mole %; in yet another embodiment, at least 90 equivalent %) of the $C_{10}$ to $C_{20}$ aliphatic dicarboxylic acids used. In other embodiments of the invention, dodecanedioic acid is one of the $C_{10}$ to $C_{20}$ aliphatic dicarboxylic acids or the only such dicarboxylic acid used in the acid component. In one embodiment, dodecanedioic acid may comprise at least 50 equivalent % (in another embodiment, at least 80 mole %; in yet another embodiment, at least 90 equivalent %) of the $C_{10}$ to $C_{20}$ aliphatic dicarboxylic acids used.

The equivalent ratio of dimerized unsaturated fatty acids to $C_{10}$ to $C_{20}$ aliphatic dicarboxylic acids in one embodiment is from about 0.15:1 to about 0.65:1, in another embodiment from about 0.2:1 to about 0.6:1. In certain embodiments of the invention, the dimerized unsaturated acid(s) and $C_{10}$ to $C_{20}$ aliphatic dicarboxylic acids together comprise at least 50 equivalent % (in another embodiment, at least 80 equivalent %; in yet another embodiment, at least 90 equivalent %) of the acid component. In one embodiment, the acid component consists essentially of or consists of dimerized unsaturated fatty acid(s), $C_{10}$ to $C_{20}$ aliphatic dicarboxylic acid(s), and monocarboxylic fatty acid(s). In other embodiments, the acid component contains less than 10 equivalent % or less than 5 equivalent %, of any dicarboxylic acid other than the dimerized unsaturated fatty acid(s) and the $C_{10}$-$C_{20}$ dicarboxylic acid(s). In still another embodiment, the acid component contains no, or essentially no, dicarboxylic acid other than the dimerized unsaturated fatty acid(s) and the $C_{10}$-$C_{20}$ dicarboxylic acid(s). Preferably, the acid component contains less than 5 equivalent % or essentially no polybasic acids (compounds containing three or more carboxylic acid groups per molecule).

To control the melt viscosity of the polyamide that is produced, it will often be desirable to also include one or more monocarboxylic acids in the mixture of components being reacted. For example, the acid component may contain an amount of monocarboxylic acid effective to provide a polyamide having a viscosity at 225° C. of not greater than 150 poise or not greater than 120 poise or not greater than 90 poise. Generally speaking, it is preferred to utilize monocarboxylic acids having relatively low volatilities, such as monobasic fatty acids (i.e., monocarboxylic acids containing 6 or more carbon atoms, preferably 8 or more carbon atoms, most preferably 10 or more carbon atoms per molecule). The monoocarboxylic acid may, for example, be a straight or branched chain, saturated or unsaturated fatty acid such as lauric acid, palmitic acid, oleic acid, stearic acid, or the like. The dimerized acid product employed as a source of the dimer acid used in the acid component may also function as a source of monocarboxylic acid, as such dimerized acid products commonly contain low levels (e.g., 1 to 15%) of one or more monocarboxylic acids. However, such monocarboxylic acids present as impurities in the dimerized acid product may be supplemented through the addition of further quantities of monoocarboxylic acid(s) in order for the total concentration of monoocarboxylic acid in the acid component to be within the desired limits (i.e., the amount required to control the polyamide melt viscosity within the desired range). The total amount of monoocarboxylic acid present during the condensation polymerization which is carried out to form the polyamide may be varied or controlled as desired to adjust the polyamide melt viscosity, but typically is from about 0.1 to about 6 equivalent % or from about 1 to about 4 equivalent %.

The amine component is comprised of at least one alkylene diamine having from 2 to 8 carbon atoms. Other types of amines may optionally also be present in the amine component. However, the $C_2$-$C_8$ alkylene diamine or mixture of $C_2$-$C_8$ alkylene diamines in one embodiment together comprises at least 50 equivalent % (in another embodiment, at least 80 equivalent %; in yet another embodiment, at least 95 equivalent %) of the amine component. In still another embodiment, the amine component consists of or consists essentially of one or more alkylene diamines having from 2 to 8 carbon atoms. In certain embodiments, the amine component is flee or essentially free of dimer amines and/or polyoxyalkylene diamines (for example, the amine component may contain less than 5 equivalent % or less than 1 equivalent % of dimer amine or polyoxyalkylene diamine).

The alkylene diamine in one embodiment corresponds to the formula:

where "n" is 2 to 8 (in one embodiment, 2 to 4), and R is hydrogen or lower (e.g., $C_1$-$C_4$) alkyl. The R groups within a single molecule may be the same or different. Straight chain alkylene diamines (where all R groups are H) are used in one embodiment of the invention, although branched chain alkylene diamines (where at least one R is an alkyl group) could also be used (either alone or in combination with one or more straight chain alkylene diamines). Thus, illustrative non-limiting examples of useful alkylene diamines include ethylenediamine, 1,2-propylenediamine, 1,3-propylenediamine, tetramethylenediamine, pentamethylenediamine, hexamethylenediamine, octamethylenediamine, 2-methyl-1,5-pentanediamine, and mixtures thereof. Preferably, "n" in the above-stated formula is at least 4 or at least 5. Where a mixture of different alkylene diamines is employed in the amine component, "n" is at least 4 or at least 5 on average. The use of alkylene diamines having a relatively high "n" value (e.g., at least 4) helps to improve the flexibility and reduce the brittleness of the polyamide obtained by condensation polymerization of the amine and acid components. Especially useful polyamides are obtained in accordance with this invention when the amine component comprises, consists essentially of, or consists of a mixture of ethylene diamine and hexamethylenediamine. In one embodiment, more hexamethylenediamine than ethylenediamine is present in the amine component. For example, the equivalent ratio of hexamethylenediamine:ethylenediamine may be from 99:1 to 60:40, or from 95:5 to 65:35, or from 90:10 to 70:30. In other embodiments of the invention, however, the amine component consists of or consists essentially of hexamethylenediamine or is comprised of at least 95 equivalent % hexamethylenediamine.

In certain embodiments, the mixture of reactants used to prepare the polyamide contains less than 15 weight percent (or less than 10 weight percent or less than 5 weight percent) lactam (in particular, caprolactam, e.g., epsilon caprolactam). For example, the reaction mixture may be free or essentially free of lactam (in particular, caprolactam, e.g., epsilon caprolactam).

In one embodiment of the present invention, a polyamide is prepared by reacting the following components:

| | |
|---|---|
| $C_{32-40}$ Dimer Acid | 16-26 or 19-23 equivalent % |
| Monobasic Fatty Acid | 0.5-6 or 1-4 equivalent % |
| Tetradecanedioic Acid | 70-80 or 73-77 equivalent % |
| Ethylenediamine | 15-25 or 18-22 equivalent % |
| Hexamethylenediamine | 75-85 or 78-82 equivalent % |

The total equivalent % of $C_{32-40}$ dimer acid, monobasic fatty acid (e.g., stearic acid), and tetradecanedioic acid may, for example, be from 95 to 100% (e.g., up to 5 equivalent % of acids other than these named acids may also form part of the acid component). The total equivalent % of ethylenediamine and hexamethylenediamine may, for example, be from 95 to 100% (e.g., up to 5 equivalent % of amines other than these named amines may also form part of the amine component). Antioxidants and/or catalysts may additionally be present.

In other embodiments of the present invention, a polyamide is prepared by reacting the following components:

| | |
|---|---|
| $C_{32-40}$ Dimer Acid | 16-26 or 19-23 equivalent % |
| Monobasic Fatty Acid | 0.5-6 or 1-4 equivalent % |
| Octadecanedioic Acid | 72-82 or 75-79 equivalent % |
| Hexamethylenediamine | 90-100 or 95-100 equivalent % |

The total equivalent % of $C_{32-40}$ dimer acid, monobasic fatty acid (e.g. stearic acid), and octadecanedioic acid may, for example, be from 95 to 100% (e.g., up to 5 equivalent % of acids other than these named acids may also form part of the acid component). Up to 10 equivalent % (alternatively, up to 5 equivalent %) of amines other than hexamethylenediamine may also form part of the amine component. Antioxidants and/or catalysts may additionally be present.

In another embodiment of the present invention, a polyamide is prepared by reacting the following components:

| | |
|---|---|
| $C_{32-40}$ Dimer Acid | 28-38 or 31-35 equivalent % |
| Monobasic Fatty Acid | 0.5-6 or 1-4 equivalent % |
| Tetradecanedioic Acid | 60-70 or 63-67 equivalent % |
| Hexamethylenediamine | 90-100 or 95-100 equivalent % |

The total equivalent % of $C_{32-40}$ dimer acid, monobasic fatty acid (e.g. stearic acid), and tetradecanedioic acid may, for example, be from 95 to 100% (e.g., tip to 5 equivalent % of acids other than these named acids may also form pail of the acid component). Up to 10 equivalent % (alternatively, up to 5 equivalent %) of amines other than hexamethylenediamine may also form part of the amine component. Antioxidants and/or catalysts may additionally be present.

In another embodiment of the present invention, a polyamide is prepared by reacting the following components:

| | |
|---|---|
| $C_{32-40}$ Dimer Acid | 18-28 or 21-25 equivalent % |
| Monobasic Fatty Acid | 0-6 or 0.5-4 equivalent % |
| Decanedioic Acid | 72-82 or 75-79 equivalent % |
| Ethylenediamine | 13-23 or 16-20 equivalent % |
| Hexamethylenediamine | 77-87 or 80-84 equivalent % |

The total equivalent % of $C_{32-40}$ dimer acid, monobasic fatty acid (e.g., stearic acid), and decanedioic acid may, for example, be from 95 to 100% (e.g., up to 5 equivalent % of acids other than these named acids may also form pail of the acid component). The total equivalent % of ethylenediamine and hexamethylenediamine may, for example, be from 95 to 100% (e.g., up to 5 equivalent % of amines other than these named amines may also form part of the amine component). Antioxidants and/or catalysts may additionally be present.

In a further embodiment of the present invention, a polyamide is prepared by reacting the following components:

| | |
|---|---|
| $C_{32-40}$ Dimer Acid | 17-27 or 19-25 equivalent % |
| Monobasic Fatty Acid | 0.5-6 or 1-4 equivalent % |
| Dodecanedioic Acid | 72-82 or 75-79 equivalent % |
| Ethylenediamine | 15-25 or 18-22 equivalent % |
| Hexamethylenediamine | 75-85 or 78-82 equivalent % |

The total equivalent % of $C_{32-40}$ dimer acid, monobasic fatty acid (e.g., stearic acid), and dodecanedioic acid may, for example, be from 95 to 100% (e.g., up to 5 equivalent % of acids other than these named acids may also form part of the acid component). The total equivalent % of ethylenediamine and hexamethylenediamine may, for example, be from 95 to 100% (e.g., up to 5 equivalent % of amines other than these named amines may also form part of the amine component). Antioxidants and/or catalysts may additionally be present.

The number of free acid groups and/or free amine groups present in the polyamide are directly related to the relative amounts of the acid component and amine component involved in the polymerization reaction and the degree of completion of the reaction. The polyamide may be either acid-terminated, amine-terminated, or contain both acid and amine terminal groups. The terminal groups of the polyamide may also be non-functional, for example an alkyl group derived from a monocarboxylic acid added to the acid component to control the molecular weight and viscosity of the polyamide. Generally speaking, polyamides in accordance with the invention that are acid-terminated tend to have better stability at elevated temperatures than the corresponding amine-terminated polyamides. However, the amine-terminated polyamides tend to exhibit better adhesion to substrate surfaces. Approximately stoichiometric amounts (e.g., a ratio of total acid to total amine groups of from about 0.9:1 to about 1.1:1, more typically from about 0.97:1 to about 1.03:1) based on the total number of available acid and amine groups may be used to prepare the polyamide resins of this invention and tile reaction conditions can be selected to ensure completion or substantial completion of the amidation (condensation) reaction.

In one embodiment of the invention, the polyamide may be the result of as complete an amidation reaction as possible between the starting acid component and the amine component. Those skilled in the art will recognize that the degree of completion of the amidation process can be determined by evaluating the acid number and the amine number of the final polymer. The polyamide may have relatively low acid and amine numbers, typically less than about 40 in total, more typically less than about 20 in total, and even more typically less than about 15 in total.

The instant polyamides may be prepared using conventional procedures and reaction conditions known to the art. It should be noted that while reference is made to acid and amine components for purposes of determining the relative amounts of each acid and amine used to prepare the polyamide, there is no need to form a separate premix of acids and a separate premix of amines, nor is it required that all reactants be charged together at the beginning of the reaction. In general, the acid and amine components may be reacted until the final product has an acid value and an amine value less than 20 (in another embodiment, less than 15), with the reaction being generally conducted at temperatures from about 100° C. to about 300° C. for from about 1 to about 8 hours. Most often the reactions will be heated from 140° to 240° C. until the theoretical amount of water is evolved. Generally several hours are required to complete the reaction. The reaction is preferably conducted under an inert atmosphere, such as nitrogen, and during the final stages of the reaction a vacuum is applied to the system to facilitate removal of the final traces of water and any other volatile materials. Applying a high vacuum will tend to result in the production of a polyamide having a higher molecular weight and correspondingly higher viscosity, which generally reduces the brittleness of the polyamide (as reflected in higher elongation values). Catalysts, such as phosphoric acid, hypophosphoric acid, sodium benzene phosphonate, sodium benzene phosphinite and the like, and/or vacuum can be used, especially in the latter part of the reaction, to yield a more complete amidation reaction and/or to increase the rate of reaction. Antifoam agents may also be utilized in order to control or suppress foaming during reaction of the components.

The polyamides obtained by the aforedescribed procedures may be used without further modification. The polyamide compositions of this invention may, however, be combined or modified with conventional additives widely known and used in the resin arts. For example, thermal stabilizers, antioxidants, UV stabilizers, plasticizers, nucleating agents, impact modifiers, tackifiers, flame retardants, antistatic agents, reinforcing agents, processing aids including mold release agents, lubricants and the like, as well as pigments, dyes, inorganic or organic fillers such as carbon black, talc, clay, mica and the like may usefully be included.

The polyamides of the present invention and compositions formulated therewith may be used in a wide variety of applications including, but not limited to, coatings, adhesives, sealants, encapsulates, films, laminates, moldings and composites. For example, the polyamide and compositions containing the polyamide may be applied to different types of substrates or may be used to join together different substrates, including webs, fibers, filaments, films, mats, foams, textiles, plastics, ceramics, and metals, as well as paper, wood and other cellulosic substrates.

The polyamides of the present invention are particularly useful as hotmelt adhesives or components of hot melt adhesives where good resistance to solvents, oil and/or fuel is needed. For example, the polyamides may be utilized in the assembly of fuel, oil or hydraulic fluid filters and the like.

The polyamide and formulations prepared therefrom can be applied to substrates using any of the methods known in the art of hot melt adhesives. For example, the polyamide or polyamide-containing composition may be heated to a temperature above its melting or liquidification point (e.g., a temperature sufficiently high to reduce the viscosity to a desired level, typically about 200 to about 250° C.) and applying the polyamide or composition to the substrate surface. If the composition is being used as a hot melt adhesive, a second substrate can be brought into contact with the polyamide or polyamide-containing composition on the surface of the first substrate before the polyamide or polyamide-containing composition completely cools and solidifies. Pressure may be applied during such contacting to ensure that a strong adhesive bond is created. The polyamide or polyamide-containing composition is thereafter permitted to cool and solidify, thereby joining together the two substrates (i.e., the two substrates are adhered to each other by the polyamide or polyamide-containing composition). Alternatively, the polyamide or polyamide-containing composition may be applied to a substrate in molten form, solidified by cooling, and then re-melted by heating prior to or even after being brought into contact with the surface of a second substrate.

EXAMPLES

A series of polyamides was prepared using different mixtures of reactant components as set forth in Table 1 (the amount of each component being expressed in parts by weight). The blended materials are heated for 90 minutes under nitrogen at 227° C. and then for an additional 60 minutes under vacuum at the same temperature to obtain the polyamide.

In each example, the acid component contained 21.3 equivalent % dimer acid, 1.7 equivalent % stearic acid, and 77.0 equivalent % of a straight chain aliphatic dicarboxylic acid while the amine component contained 20.0 equivalent % ethylenediamine and 80.0 equivalent % hexamethylenediamine. The co-acid component used was varied as follows: Example 1—decanedioic acid; Example 2—undecanedioic acid; Example 3—dodecanedioic acid; Example 4—tetradecanedioic acid; Example 5—pentadecanedioic acid; Example 6—octadecanedioic acid. Using this particular type of formulation, excellent solvent resistance could only be obtained when a dicarboxylic acid containing 14 or more carbon atoms was used together with dimer acid to form the polyamide. Satisfactory heat resistance and melt viscosities were also maintained, despite the use of the longer chain dicarboxylic acids. The polyamide of Example 4 was also found to have "Excellent" resistance to both gasoline and diesel fuel (4 days, room temperature), "Excellent" resistance to motor oil (4 days, 149° C.), "Excellent" resistance to SKYDROL aviation hydraulic fluid (10 days, 88° C.; the resistance rating dropped to "Bad" after 30 days), and "Excellent" resistance to aqueous glycol (10 days, 66° C.; the resistance rating dropped to "Good" after 30 days).

TABLE 1

| | Example | | | | | |
|---|---|---|---|---|---|---|
| | 1 | 2 | 3 | 4 | 5 | 6 |
| Dimer Acid[1] | 27.63 | 26.95 | 26.30 | 25.09 | 24.53 | 22.98 |
| Stearic Acid | 2.22 | 2.17 | 2.11 | 2.02 | 1.97 | 1.85 |
| Co-Acid | 35.77 | 37.31 | 38.77 | 41.49 | 42.76 | 46.25 |
| | (C10) | (C11) | (C12) | (C14) | (C15) | (C18) |
| Ethylenediamine | 2.70 | 2.63 | 2.57 | 2.45 | 2.40 | 2.25 |
| Hexamethylenediamine | 20.76 | 20.24 | 19.75 | 18.85 | 18.42 | 17.26 |
| Antioxidant[2] | 2.00 | 2.00 | 2.00 | 2.00 | 2.00 | 2.00 |
| Phosphoric Acid | 0.02 | 0.02 | 0.02 | 0.02 | 0.02 | 0.02 |
| Viscosity at 225° C., poise | 32 | 36 | 38 | 64 | 63 | 67 |
| Softening Point, ° C. | 199 | 186 | 192 | 188 | 179 | 180 |
| European Gasoline Resistance[3] | bad | bad | bad | excellent | mediocre | excellent |
| Gasohol Resistance[4] | poor | bad | mediocre | excellent | excellent | excellent |

Additional polyamides were prepared using the different combinations of reactants as set forth in Tables 2 and 3. For the dimer acid, stearic acid, co-acid, ethylenediamine and hexamethylene components, the first number listed in the tables is the amount of such component in equivalent % and the second number listed in the tables is the amount of each component in parts by weight. Table 2 shows that it is possible to formulate polyamides having good to excellent solvent resistance and high softening points using $C_{10}$-$C_{12}$ dicarboxylic acids. If desired, the melt viscosities of the polyamides described in Table 2 could be lowered by incorporating higher proportions of a monocarboxylic acid such as stearic acid in the mixture of reactants used to prepare the polyamides.

TABLE 2

| | Example | | | |
|---|---|---|---|---|
| | 7 | 8 | 9 | 10 |
| Dimer Acid[1] | 29.0/34.73 | 23.0/29.62 | 22.5/27.78 | 21.9/27.04 |
| Stearic Acid | 1.0/1.21 | —/— | 0.5/0.62 | 1.1/1.37 |
| Co-Acid | 70.0/30.03 | 77.0/35.51 | 77.0/38.78 | 77.0/38.77 |
| | (C10) | (C10) | (C12) | (C12) |
| Ethylenediamine | 20.0/2.67 | 18.0/2.43 | 20.0/2.57 | 20.0/2.57 |
| Hexamethylenediamine | 80.0/20.54 | 82.0/21.29 | 80.0/19.76 | 80.0/19.76 |
| Antioxidant[2] | 2.00 | 2.00 | 2.00 | 2.00 |
| Phosphoric Acid | 0.02 | 0.02 | 0.02 | 0.02 |
| Viscosity at 225° C., poise | 118 | 383 | 98 | 73 |
| Softening Point, ° C. | 195 | 202 | 193 | 194 |
| European Gasoline Resistance[3] | good | excellent | excellent | excellent |
| Gasohol Resistance[4] | good | excellent | excellent | excellent |

TABLE 3

| | Example | | | |
|---|---|---|---|---|
| | 11 | 12 | 13 | 14 |
| Dimer Acid[1] | 21.0/24.75 | 33.0/34.65 | 21.0/21.78 | 21.9/27.04 |
| Stearic Acid | 2.0/2.37 | 2.0/2.11 | 2.0/2.09 | 1.1/1.37 |
| Co-Acid | 77.0/41.5 | 65.0/31.22 | 77.0/38.78 | 77.0/38.77 |
| | (C14) | (C14) | (C18) | (C18) |
| Ethylenediamine | 20.0/2.45 | —/— | —/— | —/— |
| Hexamethylenediamine | 80.0/18.82 | 100.0/21.00 | 100.0/20.75 | 100.0/19.64 |
| Antioxidant[2] | 2.00 | 2.00 | 2.00 | 2.00 |
| Phosphoric Acid | 0.02 | 0.02 | 0.02 | 0.02 |
| Viscosity at 225° C., poise | 36 | 53 | 92 | 51 |
| Softening Point, ° C. | 187 | 194 | 193 | 186 |
| European Gasoline Resistance[3] | excellent | excellent | excellent | excellent |
| Gasohol Resistance[4] | excellent | excellent | excellent | excellent |

[1] EMPOL 1008 hydrogenated dimer acid, obtained from Cognis Corporation (2-6% monobasic acids, 90-98% dibasic acids, 1-5% polybasic acids, saponification value 196-203)

[2] NAUGARD 445 amine antioxidant, obtained from Uniroyal Chemical

[3] tested using mixture of 42.3% toluene, 4.2% ethanol, 15.0% methanol, 25.3% isooctane, 12.7% diisobutylene and 0.5% water; 4 days at room temperature

[4] 80% gasoline, 20% ethanol; 4 days at room temperature

Solvent resistance was measured by submerging a test specimen of the polyamide having a thickness of 50 mil in the solvent at a specified temperature for a certain tine. The solvent resistance was rated as follows:

Excellent=no cracking, specimen remains flexible
Good=minor cracking on edge, specimen remains flexible
Mediocre=some major cracking, specimen remains flexible
Poor=major flaking and cracking, specimen becomes brittle
Bad=specimen completely broken into small pieces and partially dissolved The polyamide melt viscosity may be measured in accordance with ASTM D3236-88 using a Model DVI+ Brookfield Viscometer (obtained from Brookfield Engineering Laboratories, Inc., Stoughton, Mass.).

Softening point may be measured as a ring and ball softening point in accordance with ASTM E 28-99.

What is claimed is:

1. A polyamide which is the reaction product of a) an acid component comprising at least one unsaturated fatty acid having from 12 to 24 carbon atoms which is dimerized and at least one aliphatic dicarboxylic acid having from 10 to 20 carbon atoms and b) an amine component comprising at least one alkylene diamine having from 2 to 8 carbon atoms; wherein the aliphatic dicarboxylic acid having from 10 to 20 carbon atoms comprises at least 50 equivalent % of the polyamide.

2. A polyamide according to claim 1 wherein the acid component comprises at least one unsaturated fatty acid having from 16 to 20 carbon atoms which is dimerized.

3. A polyamide according to claim 1 wherein the acid component comprises at least one aliphatic dicarboxylic acid selected from the group consisting of decanedioic acid, undecanedioic acid, dodecanedioic acid, tetradecanedioic acid and octadecanedioic acid.

4. A polyamide according to claim 1 wherein said at least one unsaturated fatty acid having from 12 to 24 carbon atoms which is dimerized has an iodine value less than 20.

5. A polyamide according to claim 1 wherein the at least one unsaturated fatty acid having from 12 to 24 carbon atoms which is dimerized is prepared using one or more fatty acids selected from the group consisting of oleic acid, linoleic acid, linolenic acid, and mixtures thereof.

6. A polyamide according to claim 1 wherein the acid component is additionally comprised of at least one $C_{12}$ to $C_{24}$ monocarboxylic acid.

7. A polyamide according to claim 1 wherein the acid component consists essentially of said at least one unsaturated fatty acid having from 12 to 24 carbon atoms which is dimerized, at least one aliphatic dicarboxylic acid having from 10 to 20 carbon atoms, and at least one $C_{10}$ to $C_{24}$ monoocarboxylic acid.

8. A polyamide according to claim 1 wherein the amine component consists essentially of ethylenediamine and hexamethylenediamine.

9. A polyamide according to claim 1 wherein the amine component comprises ethylene diamine and hexamethylenediamine and wherein the equivalent ratio of hexamethylene diamine:ethylene diamine is from 95:5 to 65:35.

10. A polyamide according to claim 1 wherein the amine component consists essentially of one or more alkylene diamines having the formula $H_2N-(CH_2)_n-NH_2$ wherein n is at least 5 on average.

11. A polyamide according to claim 1 wherein said acid component does not contain more than 5 equivalent % total of dicarboxylic acids other than said one or more dicarboxylic acid having from 10 to 20 carbon atoms and said at least one unsaturated fatty acid having from 12 to 24 carbon atoms which is dimerized.

12. A polyamide according to claim 1 wherein said at least one unsaturated acid having from 12 to 24 carbon atoms which is dimerized and said at least one aliphatic dicarboxylic acid having from 10 to 20 carbon atoms together comprise at least 80 equivalent % of the acid component.

13. A polyamide according to claim 1 wherein said at least one $C_2$-$C_8$ alkylene diamine comprises at least 80 equivalent % of the amine component.

14. A polyamide according to claim 1 wherein the equivalent ratio of said at least one unsaturated fatty acid having from 12 to 24 carbon atoms which is dimerized to said at least one aliphatic dicarboxylic acid having from 10 to 20 carbon atoms is from about 0.2:1 to about 0.6:1.

15. A polyamide according to claim 1 which is the reaction product of a) 16 to 26 equivalent % $C_{32-40}$ dimer acid, b) 0.5 to 6 equivalent % monobasic fatty acid, c) 70 to 80 equivalent % tetradecanedioic acid, d) 15 to 25 equivalent % ethylenediamine, and e) 75 to 85 equivalent % hexamethylenediamine, wherein the total of a), b), and c) is from 90 to 100 equivalent % and the total of d) and e) is from 90 to 100 equivalent %.

16. A polyamide according to claim 1 which is the reaction product of a) 16 to 26 equivalent % $C_{32-40}$ dimer acid, b) 0.5 to 6 equivalent % monobasic fatty acid, c) 72 to 82 equivalent % octadecanedioic acid, and d) 90 to 100 equivalent % hexamethylenediamine, wherein the total of a), b), and c) is from 90 to 100 equivalent %.

17. A polyamide according to claim 1 which is the reaction product of a) 28 to 38 equivalent % $C_{32-40}$ dimer acid, b) 0.5 to 6 equivalent monobasic fatty acid, c) 60 to 70 equivalent % tetradecanedioic acid, and d) 90 to 100 equivalent % hexamethylenediamine, wherein the total of a), b), and c) is from 90 to 100 equivalent %.

18. A polyamide according to claim 1 which is the reaction product of a) 18 to 28 equivalent % $C_{32-40}$ dimer acid, b) 0.5 to 6 equivalent % monobasic fatty acid, c) 72 to 82 equivalent % decanedioic acid, d) 13 to 23 equivalent % ethylenediamine, and e) 77 to 87 equivalent % hexamethylenediamine, wherein the total of a), b), and c) is from 90 to 100 equivalent % and the total of d) and e) is from 90 to 100 equivalent %.

19. A polyamide according to claim 1 which is the reaction product of a) 17 to 27 equivalent % $C_{32-40}$ dimer acid, b) 0.5 to 6 equivalent % monobasic fatty acid, c) 72 to 82 equivalent % dodecanedioic acid, d) 15 to 25 equivalent % ethylenediamine, and e) 75 to 85 equivalent % hexamethylenediamine, wherein the total of a), b), and c) is from 90 to 100 equivalent % and the total of d) and e) is from 90 to 100 equivalent %.

20. An article comprising a first substrate joined to a second substrate by an adhesive, wherein said adhesive is comprised of the polyamide of claim 1.

21. The article of claim 20, wherein said article is a filter.

22. A method of adhering a first substrate to a second substrate, said method comprising applying an adhesive in molten form comprised of the polyamide of claim 1 to a surface of said first substrate to form an adhesive-coated surface, contacting said adhesive-coated surface with a surface of said second substrate while said adhesive is still in molten form, and cooling said adhesive until said adhesive solidifies.

23. The polyamide of claim 1 wherein said at least one unsaturated fatty acid having from 12 to 24 carbon atoms which is dimerized is hydrogenated to 90% or more.

24. A polyamide which is the reaction product of a) an acid component comprising at least one saturated fatty acid having from 12 to 24 carbon atoms which is dimerized and at least one aliphatic dicarboxylic acid having from 10 to 20 carbon atoms and b) an amine component comprising at least one alkylene diamine having from 2 to 8 carbon atoms; wherein the aliphatic dicarboxylic acid having from 10 to 20 carbon atoms comprises at least 50 equivalent % of the polyamide.

25. A polyamide according to claim 24 which is the reaction product of a) 16 to 26 equivalent % $C_{32-40}$ dimer acid, b) 0.5 to 6 equivalent % monobasic fatty acid, c) 70 to 80 equivalent % tetradecanedioic acid, d) 15 to 25 equivalent % ethylenediamine, and e) 75 to 85 equivalent % hexamethylenediamine, wherein the total of a), b), and c) is from 90 to 100 equivalent % and the total of d) and e) is from 90 to 100 equivalent %.

26. A polyamide according to claim 24 which is the reaction product of a) 16 to 26 equivalent % $C_{32-40}$ dimer acid, b) 0.5 to 6 equivalent % monobasic fatty acid, c) 72 to 82 equivalent % octadecanedioic acid, and d) 90 to 100 equivalent % hexamethylenediamine, wherein the total of a), b), and c) is from 90 to 100 equivalent %.

27. A polyamide according to claim 24 which is the reaction product of a) 28 to 38 equivalent % $C_{32-40}$ dimer acid, b) 0.5 to 6 equivalent % monobasic fatty acid, c) 60 to 70 equivalent % tetradecanedioic acid, and d) 90 to 100 equivalent % hexamethylenediamine, wherein the total of a), b), and c) is from 90 to 100 equivalent %.

28. A polyamide according to claim 24 which is the reaction product of a) 18 to 28 equivalent % $C_{32-40}$ dimer acid, b) 0.5 to 6 equivalent % monobasic fatty acid, c) 72 to 82 equivalent % decanedioic acid, d) 13 to 23 equivalent % ethylenediamine, and e) 77 to 87 equivalent % hexamethylenediamine, wherein the total of a), b), and c) is from 90 to 100 equivalent % and the total of d) and e) is from 90 to 100 equivalent %.

29. A polyamide according to claim 24 which is the reaction product of a) 17 to 27 equivalent % $C_{32-40}$ dimer acid, b) 0.5 to 6 equivalent % monobasic fatty acid, c) 72 to 82 equivalent % dodecanedioic acid, d) 15 to 25 equivalent % ethylenediamine, and e) 75 to 85 equivalent % hexamethylenediamine, wherein the total of a), b), and c) is from 90 to 100 equivalent % and the total of d) and e) is from 90 to 100 equivalent %.

30. The polyamide of claim 24 wherein the polyamide has a softening point of at least 182° C. using a ring and ball in accordance with ASTM E 28-99.

31. The polyamide of claim 24 wherein a test sample of the polyamide having a thickness of 50 mil remains flexible after submersion in a solvent comprising gasoline and ethanol for at least 4 days at room temperature.

32. The polyamide of claim 24 wherein a test sample of the polyamide having a thickness of 50 mil remains flexible after submersion in a gasoline mixture comprising octane and one or more of the following: toluene, ethanol, methanol and diisobutylene for at least 4 days at room temperature.

33. The polyamide of claim 24 wherein the polyamide has a Shore A hardness of greater than 90 and wherein a micro dogbone sample of the polyamide having a thickness of 50 mil exhibits an elongation of at least 50%.

34. The polyamide of claim 24 wherein the polyamide has a melt viscosity at 225° C. of less than 150 poise as measured in accordance with ASTM D3236-88.

35. An article comprising a first substrate joined to a second substrate by an adhesive, wherein said adhesive is comprised of the polyamide of claim 24.

36. The article of claim 35, wherein said article is a filter.

37. A method of adhering a first substrate to a second substrate, said method comprising applying an adhesive in molten form comprised of the polyamide of claim 24 to a surface of said first substrate to form an adhesive-coated surface, contacting said adhesive-coated surface with a surface of said second substrate while said adhesive is still in molten form, and cooling said adhesive until said adhesive solidifies.

* * * * *